(12) United States Patent
Otto (10) Patent No.: US 9,186,232 B1
(45) Date of Patent: Nov. 17, 2015

(54) HYPERBARIC OXYGEN THERAPY CHAMBER AND SYSTEM FOR USE IN VETERINARY MEDICINE

(71) Applicant: Edgar Otto, Boca Raton, FL (US)

(72) Inventor: Edgar Otto, Boca Raton, FL (US)

( * ) Notice: Subject to any disclaimer, the term of this patent is extended or adjusted under 35 U.S.C. 154(b) by 277 days.

(21) Appl. No.: 13/767,128

(22) Filed: Feb. 14, 2013

Related U.S. Application Data (60) Provisional application No. 61/598,534, filed on Feb. 14, 2012.

(51) Int. Cl.
| | |
|---|---|
| A61G 10/00 | (2006.01) |
| A61G 10/02 | (2006.01) |
| A61G 10/04 | (2006.01) |
| A61D 7/00 | (2006.01) |
| A61B 5/00 | (2006.01) |
| A61D 3/00 | (2006.01) |
| A61M 16/00 | (2006.01) |

(52) U.S. Cl.
CPC ............... *A61D 7/00* (2013.01); *A61B 5/0013* (2013.01); *A61B 5/0077* (2013.01); *A61D 3/00* (2013.01); *A61G 10/026* (2013.01); *A61M 16/0051* (2013.01)

(58) Field of Classification Search
CPC ..... A61G 10/026; A61G 1/013; A01K 1/031; A61D 7/04; A61D 3/00; A62B 31/00; A62B 2503/40; A63B 2208/053; A61M 2250/00; B63C 11/32; B63C 11/325; A47B 17/03; A47B 21/03; A61B 3/0083

USPC ............. 128/202.12, 202.13, 202.14, 202.15, 128/202.16, 205.26; 5/81.1 HS; 119/753; 600/21, 22
See application file for complete search history.

(56) References Cited

U.S. PATENT DOCUMENTS

| | | | | |
|---|---|---|---|---|
| 3,587,574 A | * | 6/1971 | Merecer | 128/205.26 |
| 4,085,705 A | | 4/1978 | Gland | |
| 4,227,524 A | * | 10/1980 | Galerne | 128/205.26 |

(Continued)

OTHER PUBLICATIONS

Rech (A Proposal of Multiplace Hyperbaric Chamber for Animal Experimentation and Veterinary Use, ACTA Cirurgica Brasileira—vol. 23 (4) 2008, http://www.ncbi.nlm.nih.gov/pubmed/18641810, Accessed Jan. 6, 2015).*

*Primary Examiner* — Lynne Anderson
*Assistant Examiner* — Peter S Vasat
(74) *Attorney, Agent, or Firm* — Mark D. Bowen; Malin Haley DiMaggio & Bowen, P.A.

(57) ABSTRACT

Systems and methods for use in providing hyperbaric oxygen therapy ("HBOT") sessions to veterinary patients includes providing HBOT chambers specifically adapted for use with veterinary patients. HBOT chambers are adapted with a rail mounted platform upon which one or more animals may be supported and confined within an enclosure during the application of HBOT. Viewing ports are provided at the appropriate level to allow the pets being treated to see out from their position within the chamber. The system is provided with a closed circuit video system including a plurality of chamber mounted cameras configured allow for remote monitoring of the animals within the chamber, and a room mounted camera configured to allow for remote monitoring of the chamber and surrounding environment. Remote central station monitoring allows for widespread deployment of hyperbaric chambers in accordance with a business method wherein revenue is generated on per-use and/or per-patient basis.

3 Claims, 9 Drawing Sheets

(56) References Cited

U.S. PATENT DOCUMENTS

| | | |
|---|---|---|
| 4,305,347 A | 12/1981 | Hemenway |
| 4,365,590 A | 12/1982 | Ruggieri |
| 4,577,628 A | 3/1986 | Hickman |
| 4,727,870 A | 3/1988 | Krasle |
| 4,941,431 A | 7/1990 | Anderson |
| 5,109,837 A | 5/1992 | Gamow |
| 6,352,076 B1 | 3/2002 | French |
| 6,443,148 B1 | 9/2002 | Rodocker |
| 6,497,231 B1 | 12/2002 | White |
| 7,402,137 B2 | 7/2008 | Lomask |
| 7,665,463 B2 | 2/2010 | Grauke |
| 2007/0175475 A1* | 8/2007 | Grauke .................. 128/205.26 |

\* cited by examiner

HYPERBARIC OXYGEN THERAPY CHAMBER AND SYSTEM FOR USE IN VETERINARY MEDICINE

CROSS REFERENCE TO RELATED APPLICATIONS

This application claims the benefit of provisional U.S. Patent Application Ser. No. 61/598,534, filed on Feb. 14, 2012.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all rights whatsoever.

BACKGROUND OF THE INVENTION

1. Field of the Invention

The present invention generally relates to hyperbaric oxygen therapy chambers, and more particularly to a hyperbaric oxygen therapy chamber and system specifically adapted for use in the field of veterinary medicine.

2. Description of Related Art

Hyperbaric medicine, also known as hyperbaric oxygen therapy ("HBOT"), is the medical use of oxygen at a pressure higher than atmospheric pressure. HBOT involves the use of a pressure chamber (or hyperbaric chamber), adapted with means for delivering 100% oxygen. Operation is performed to a predetermined schedule by trained personnel who monitor the patient. HBOT was originally used in the treatment of decompression sickness, but has been found to have wide ranging beneficial effects.

The typical type of hyperbaric chamber used in HBOT is a hard shelled pressure vessel having an entry hatch for patients, viewing ports and/or closed circuit television to allow technicians or medical staff outside the chamber to monitor the patient inside the chamber, and a control panel outside the chamber that functions to control the flow of oxygen and pressure within the chamber. Hyperbaric chambers range in size from semi-portable, one-patient units to room sized units that can treat a number of patients simultaneously. The hyperbaric chamber is typically pressurized to 2 atmospheres. HBOT allows patients to breathe pure oxygen inside a controlled and high-pressure environment. This environment has been found to increase the oxygen that is supplied to the body, and results in the creation of conditions which support healthy cell growth and functions.

While most hyperbaric chambers are designed for use with human patients, HBOT chambers have been designed for veterinary medicine use. For example, U.S. Pat. No. 7,665,463, issued to Grauke, discloses a large animal hyperbaric oxygen chamber that is large enough for a horse. The chamber includes a number of portholes (114) that are arranged so that the subject within the chamber may be viewed. U.S. Pat. No. 6,443,148, issued to Rodocker, discloses a hyperbaric oxygen therapy system having a generally horizontal extension chamber (14) within which a user or multiple users, either human or animal, receive hyperbaric treatment.

While the background art reveals several advancements in the development of HBOT chambers and systems intended for use in veterinary medicine, those advancements are burdened by a number of limitations and disadvantages that have prevented widespread use and commercial success. Accordingly, there exists a need in the art of veterinary medicine for improved systems and methods for providing hyperbaric oxygen therapy.

BRIEF SUMMARY OF THE INVENTION

The present invention overcomes the limitations and disadvantages present in the art of hyperbaric oxygen therapy in the field of veterinary medicine by providing a hyperbaric chamber specifically adapted for use in the simultaneous treatment of multiple animals. The present invention further provides advancements in remote electronic monitoring of system use and performance. A hyperbaric chamber in accordance with the present invention comprises a pressure vessel having a first end adapted with an openable hatch, and a second closed end. Within the chamber is a rail mounted platform or bed upon which one or more animals may be supported. The animals are preferably confined within an enclosure during the application of HBOT. The rail mounted bed is slidably adjustable between a first position, wherein the bed is fully retracted within the chamber, and a second position, wherein the bed is slidably extended at least partially out of the chamber to facilitate insertion and removal of animals confined in generally transparent crates. The bed is further adapted with a locking mechanism for securing the bed in the first position to prevent the animals being treated from moving the bed. Viewing ports are provided at the appropriate level to allow the pets being treated to see out from their position within the chamber. The system is provided with a closed circuit video system including a plurality of chamber mounted cameras configured allow for remote monitoring the patients (i.e. animals or pets) within the chamber, and a room mounted camera configured to allow for remote monitoring of the chamber and surrounding environment. Remote central station monitoring allows for widespread deployment of hyperbaric chambers in accordance with a business method wherein revenue is generated on per use and/or per patient basis.

Accordingly, it is an object of the present invention to provide advancements in the field of veterinary hyperbaric oxygen treatment.

Another object of the present invention is to provide a hyperbaric chamber specifically adapted for use in treating animals.

Still another object of the present invention is to provide a system of remote monitoring of a hyperbaric chamber and patients being treated therein.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

With reference now to the drawings, FIGS. 1-12 depict and illustrate a preferred embodiment of a hyperbaric oxygen therapy system, generally referenced as 10, specifically adapted for use in the hyperbaric oxygen therapy treatment of multiple animals simultaneously in accordance with the present invention.

Hyperbaric oxygen therapy system 10 preferably includes a generally cylindrical pressure vessel 12 which is horizontally disposed so as to define a top forming an uppermost cylindrical surface and a bottom forming lowermost cylindrical surface. Pressure vessel 12, and particularly the bottom portion thereof, is mounted to and supported by a base 14. Pressure vessel 12 is preferably fabricated from welded steel, however, any suitable material and fabrication technique are considered within the scope of the present invention. Base 14 preferably comprises cabinet structure having a door 16, and is adapted with wheels 18 to facilitate portability and ease of transport. Pressure vessel 12 is in fluid communication with a source of pressurized oxygen (not shown) as is customary in the art.

Figure 1:
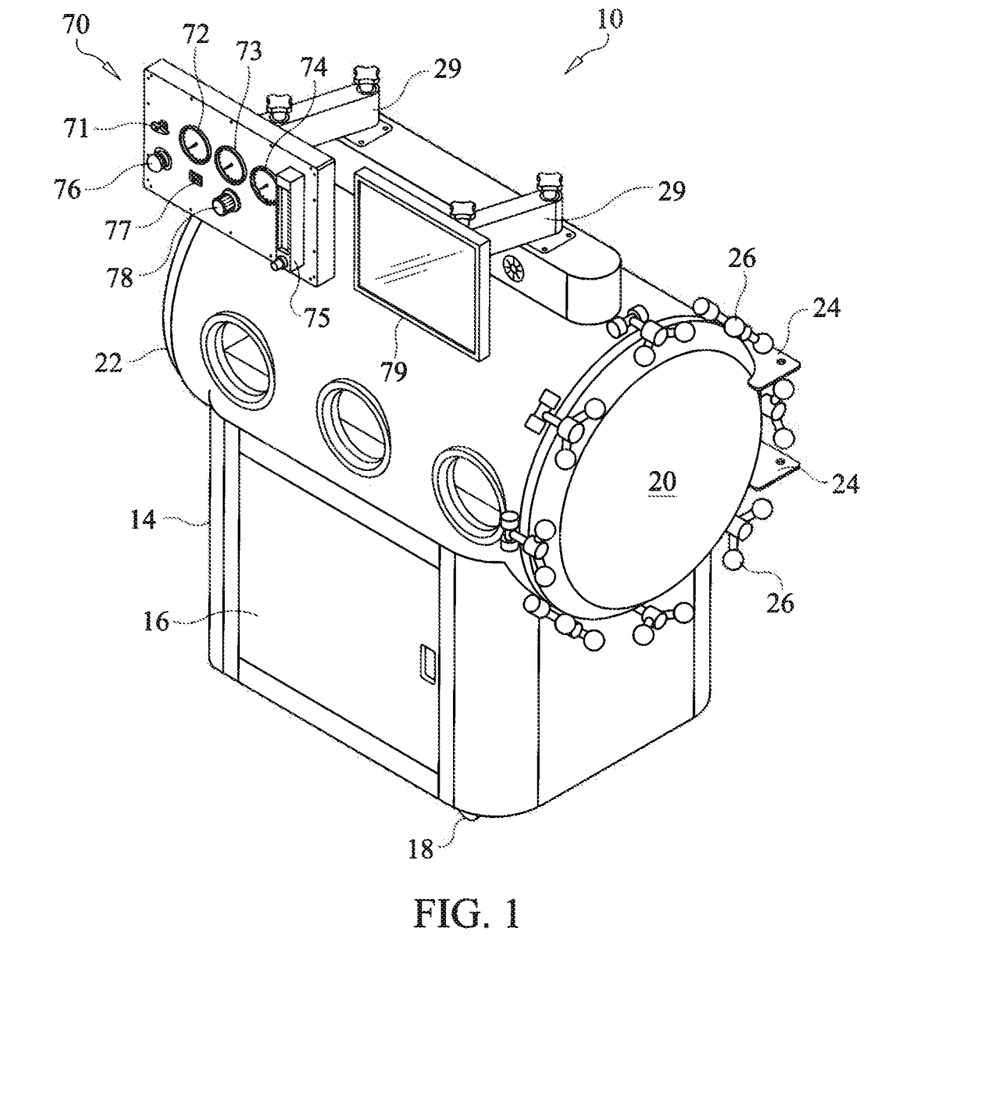
FIG. 1 is a top perspective view of a hyperbaric oxygen therapy chamber for use in veterinary medicine applications in accordance with the present invention.
Figure 2:
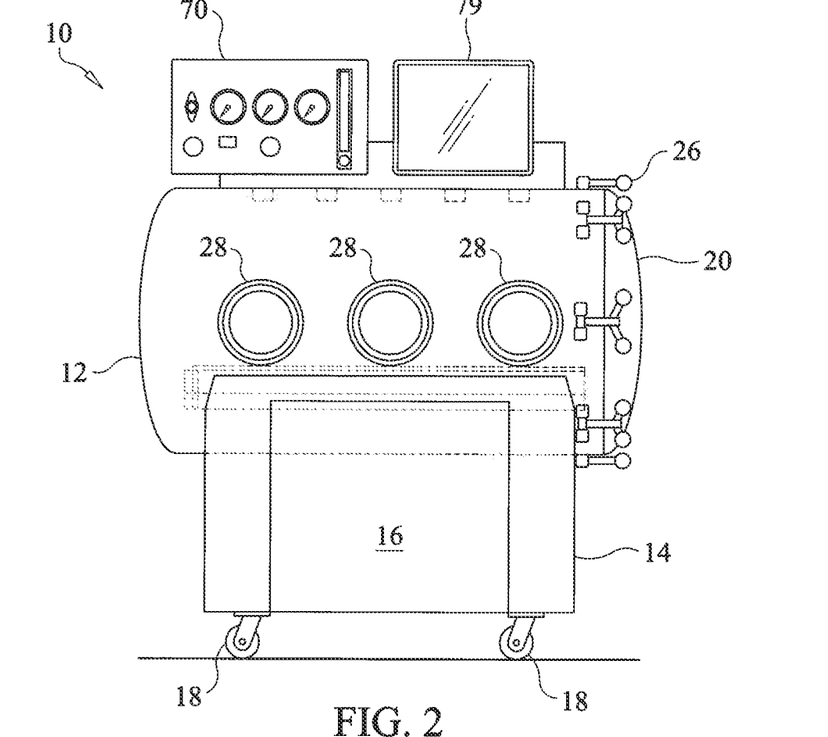
FIG. 2 is a front view thereof.
Figure 3:
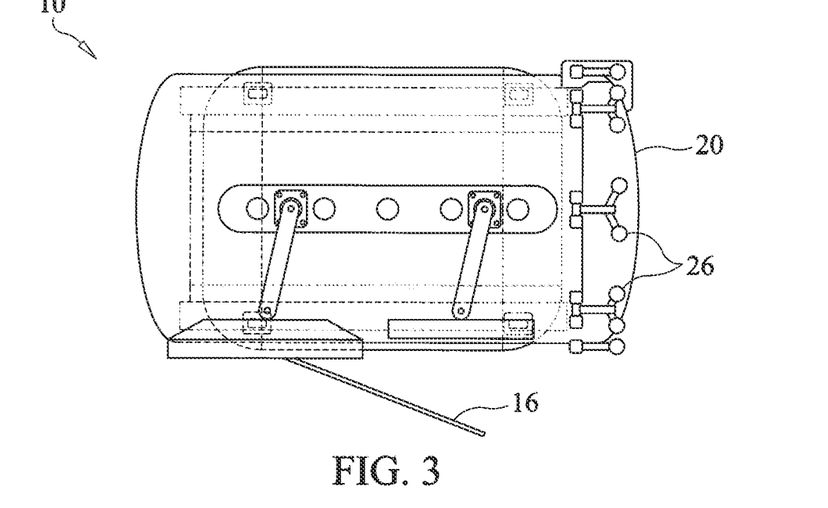
FIG. 3 is a top view thereof.
Figure 4:
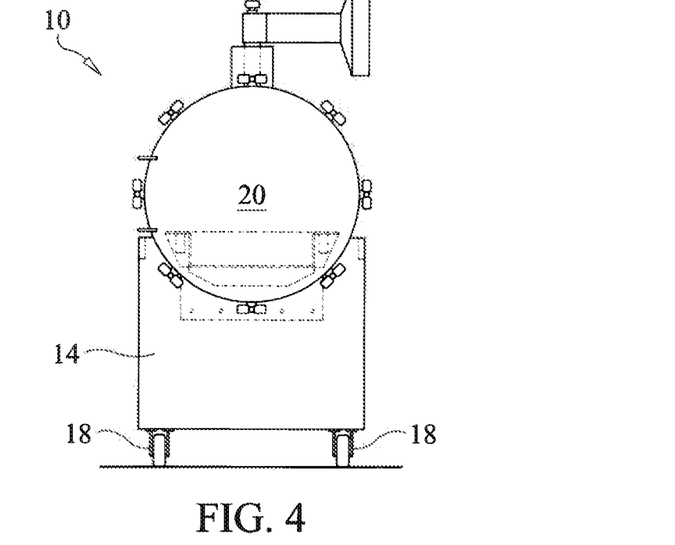
FIG. 4 is a left side view thereof.
Figure 6:
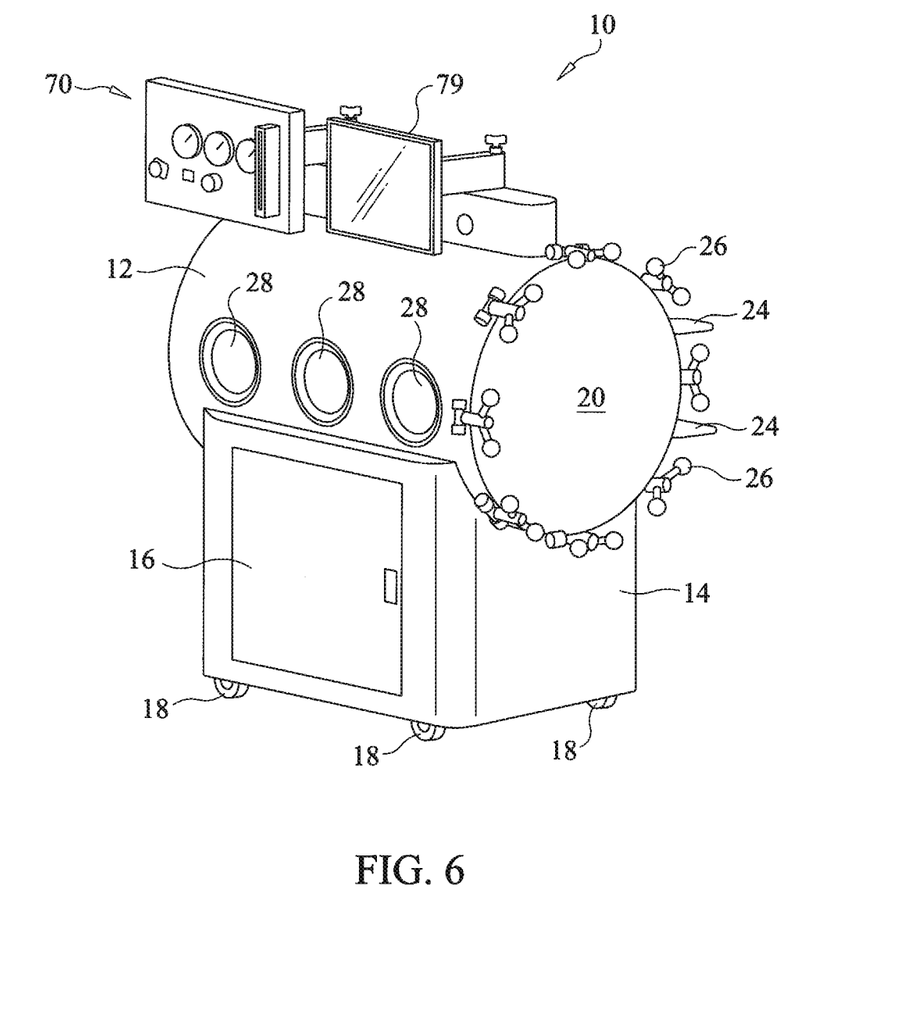
FIG. 6 is a front perspective view of a hyperbaric chamber in accordance with the present invention with the access hatch in the closed configuration.
Figure 7:
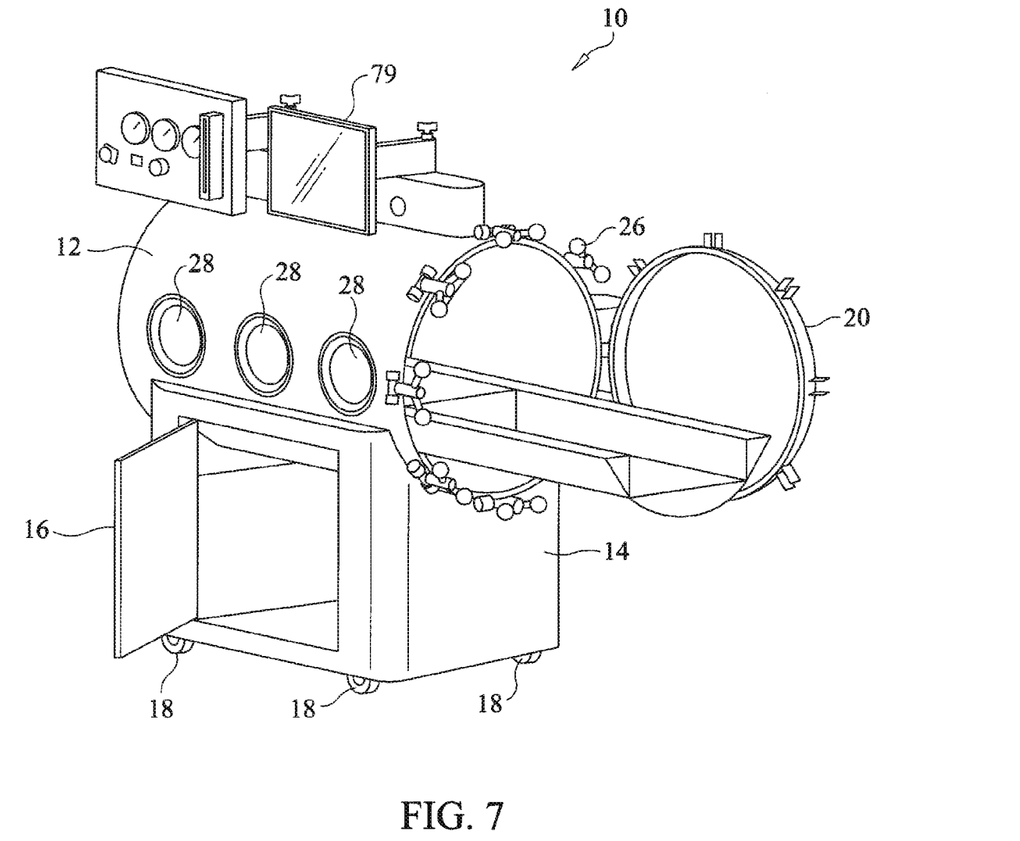
FIG. 7 is a front perspective graphic illustration of a hyperbaric chamber in accordance with the present invention with the access hatch in the open configuration and with the patient bed extended.

Pressure vessel 12 includes a first open end adapted with a door or hatch 20, and an opposing closed second end 22. As used herein the term "hatch" shall refer to a closure structure, such as an openable and closable door or other suitable closure structure. Hatch 20 is preferably pivotally mounted to pressure vessel 12 via hinges 24 that allow hatch 20 to generally freely swing from a closed configuration as illustrated in FIG. 6, to an open configuration as illustrated in FIG. 7. Hatch 20 is preferably secured in the closed position by a plurality of latches 26 so as to maintain a pressure resistant seal between hatch 20 and the open end of pressure vessel 12 when hatch 20 is in the closed configuration. In the embodiment depicted in FIGS. 1-3, hatch 20 comprises a structure that is convex, when viewed from the exterior. The present inventor, however, contemplates an alternate embodiment, wherein hatch 20 is concave when viewed from the exterior. Providing a hatch that is generally concave, when viewed from the exterior, is advantageous in that it minimizes the overall dimensions (e.g. length) of the hyperbaric chamber 10. As should be apparent, the closed end 22 is also convex when viewed from the exterior as seen in FIGS. 1-3, but may alternately be concave to further reduce overall dimensions. Hatch 20 and hinges 24 may be fabricated at the factory such that hatch 20 is factory installed in either a left-hand out-swing or a right-hand out-swing. In an alternate embodiment (not shown), hyperbaric chamber 10 may be adapted with dual sets of hinges 24 to allow hatch 20 to be reversed in the field between a left-hand out-swing configuration and a right-hand out-swing configuration.

A further significant aspect of the present invention relates to providing a hyperbaric oxygen therapy system 10 with a pressure vessel 12 having windows or viewing ports 28 that are specifically positioned so as to allow the patient (e.g. dog) to peer out from the chamber, while also allowing persons outside the chamber to view the patient. In accordance with this aspect of the present invention, view ports 28 are specifically positioned to provide for the comfort of animal patients disposed within pressure vessel 12 while undergoing treatment. More particularly, as non-opening, porthole-style view ports 28 are generally horizontally disposed and positioned approximately midway between the top and bottom of the horizontally disposed cylindrical wall at a position that generally corresponds with the intersection of the pressure vessel circumferential wall and a line corresponding to a generally horizontally disposed bisecting line (e.g. diameter). It is important that view ports 28 are specifically positioned to allow animals and pets, such as dogs and cats, to be able to view the outside the chamber, whereby the pet may view its owner, so as to keep the animals calm during treatment. The present inventor has thus positioned view ports 28, relatively low, at approximately 90-degrees and/or 270-degrees (with 0-degrees/360-degrees as a top reference), as compared with chambers of the prior art wherein the view ports are disposed on the top, to allow pets to see generally horizontally outward, as opposed to upward. This position allows pets to easily see outward from pressure vessel 12 through view ports 28 while undergoing treatment.

FIGS. 6-9 illustrate another significant aspect of the present invention, namely a slidably mounted platform or bed system, referenced as 30, upon which one or more crated, caged, or confined animals may be supported. As illustrated in FIGS. 6 and 7, bed 30 is slidably adjustable between a first position wherein the bed is fully retracted within the chamber, and a second position wherein the bed is slidably extended at least partially out of the chamber to facilitate insertion and removal of animals which are confined in generally transparent crates as more fully discussed herein.

Figure 8:
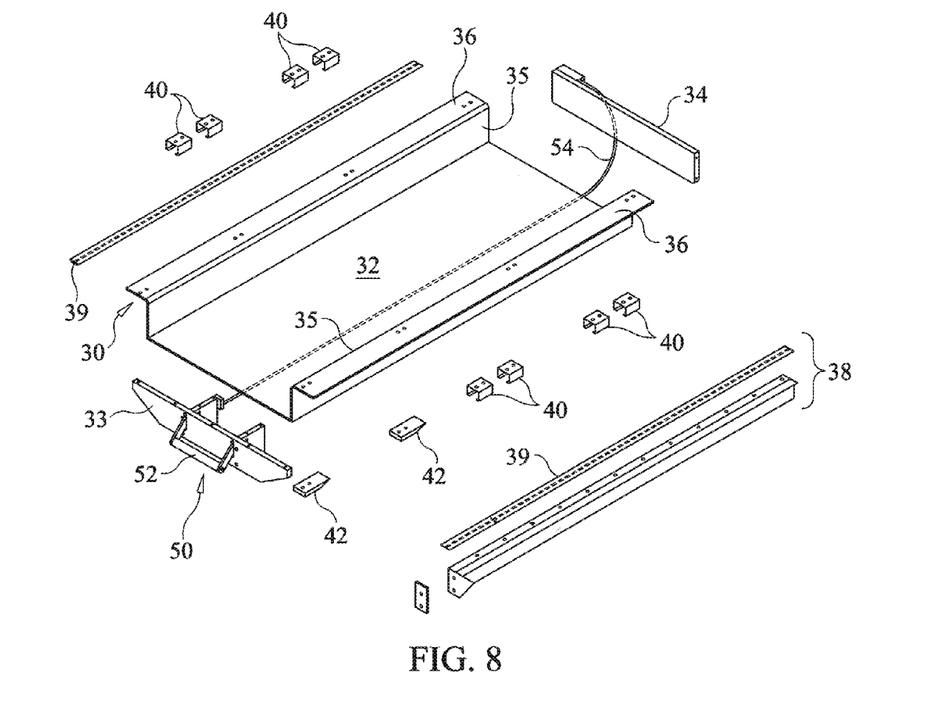
FIG. 8 is an exploded view of the patient bed assembly for a hyperbaric chamber in accordance with the present invention.
Figure 9:
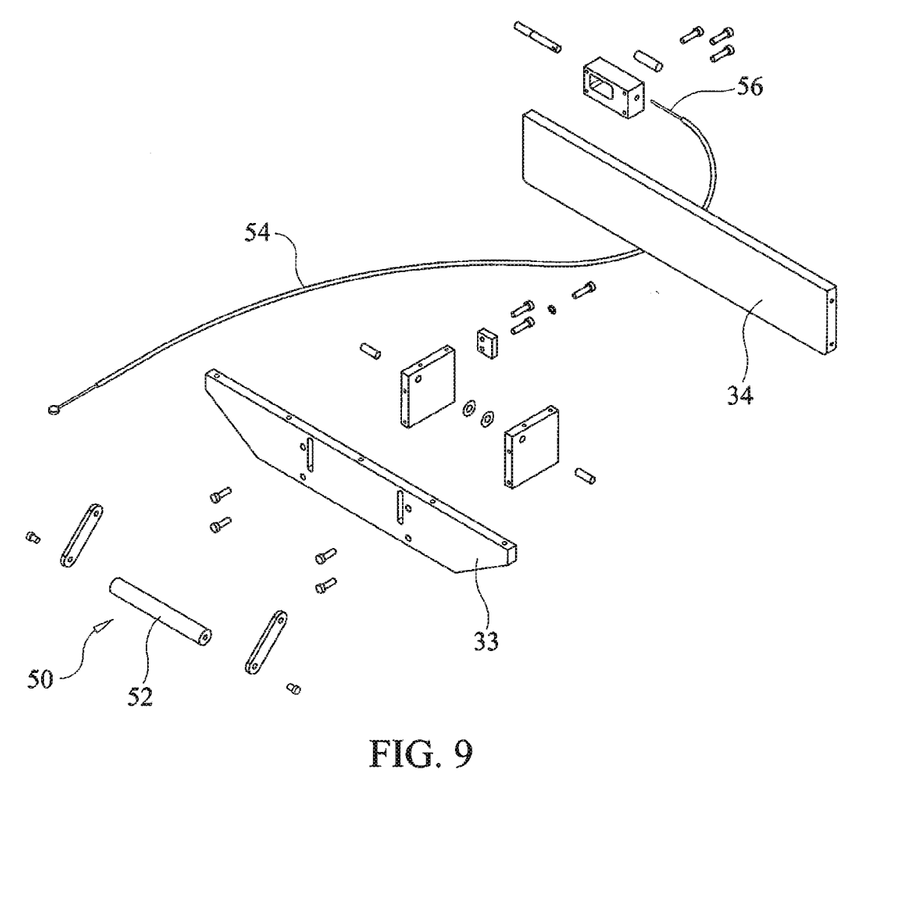
FIG. 9 is a partial detailed exploded view of the latch mechanism thereof.

FIGS. 8 and 9 provide detailed exploded views of bed 30 and various sliding and latching systems and mechanisms in accordance with a preferred embodiment of the present invention. As best seen in FIG. 8, bed system 30 includes a slidably mounted platform 32 having a front end 33, a rear end 34, and opposing left and right sides, each referenced as 35. Sides 35 each include a laterally projecting flange 36 which functions as load bearing structure. More particularly, each projecting flange 36 is adapted to slidably engage a corresponding rail assembly 38. One or more clips 40 are attached to the underside of each flange 36, and functions as a mount for a suitable, preferably low friction and/or self lubricating, plastic insert material 42 having a low coefficient of static and dynamic friction. A suitable inset material includes nylon. Clips 40 receive a mating top portion 39 of rail assembly 38 in slidable engagement therewith. As should be apparent, plastic insert material 42 slides over the top portion 39 of rail assembly 38, and the bear the weight of bed 30 while allowing bed 30 the easily slide back and forth. The use of plastic insert material 42 is important as it allows sliding engagement while avoiding spark inducing metal-to-metal contact.

FIG. 9 depicts an exploded view of a latching mechanism, generally referenced as 50, for bed system 30. A handle 52 is pivotally mounted to the front end 33 of platform 32, and pivotally movable between a normally disposed lower position and an upper position. Handle 52 is connected to a cable 54 terminating in an anchor pin 56 disposed at the rear end 34 of platform 32. When handle 52 is disposed in the lower position, anchor pin 56 is disposed in a generally extended configuration. Conversely, when handle 52 is urged upward by a user to the upper position anchor pin 56 is disposed in a generally retracted configuration. Anchor pin 56 preferably functions as a stop by engaging a stop block or other rigid pressure vessel structure (not shown) when disposed in the extended configuration. Preferably at least two stop positions are provided, including a stop position corresponding to the first bed position wherein the bed is fully retracted within the chamber, and a stop position corresponding to the second bed position wherein the bed is slidably extended at least partially out of the chamber. In addition, intermediate stop positions may also be incorporated. It is important to fix platform 42 within pressure vessel 12 when in use to prevent the animal(s) being treated from causing movement of platform 32 during a treatment session.

Figure 5:
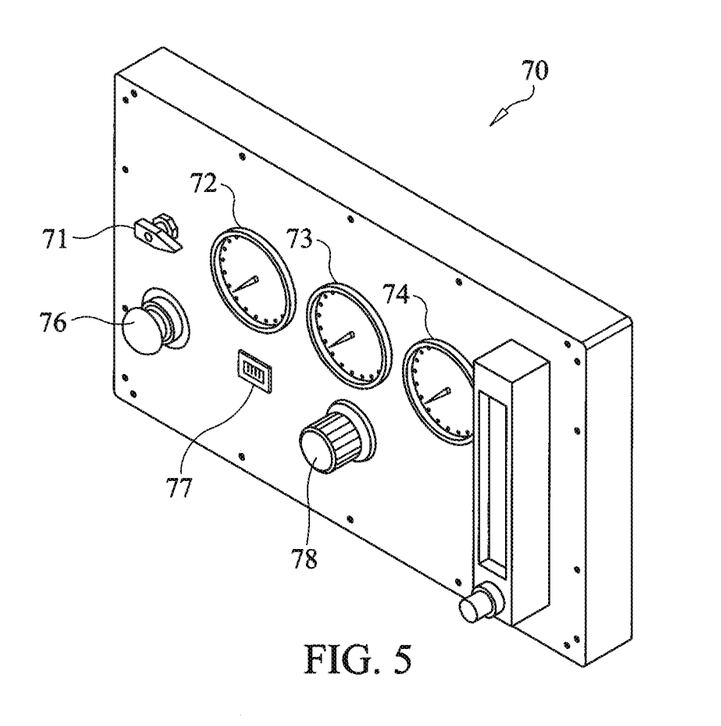
FIG. 5 is a perspective view of a control panel for a hyperbaric oxygen therapy chamber in accordance with the present invention.

FIG. 5 depicts a control panel, generally referenced as 70, for use in the on-site monitoring and operation of a hyperbaric chamber of the present invention. Control panel 70 includes an oxygen supply "on/off" switch 71, a line pressure gauge 72, a regulated pressure gauge 73, a chamber pressure gauge 74, a flow meter 75, an emergency shut-off switch 76, a use counter 77, and a flow regulator knob 78. As should be apparent, the exact configuration of control panel 70 as well as the type of controls and gauges thereon may vary provided sufficient controls and gauges are present to enable chamber 12 to operate as a HBOT unit. In addition, an electronic display 79 is provided to allow the operator to view the patients while undergoing treatment. Control panel 70 and display 79 are each attached to pressure vessel 12 in cantilevered fashion by swing arms 29 that allow for adjustment thereof. Each swing arm 29 includes a pair of set-screws 29A that allow for side-to-side pivotal adjustment of the swing arm as well as pivotal/angular adjustment of panel 70 and display 79.

Figure 10:
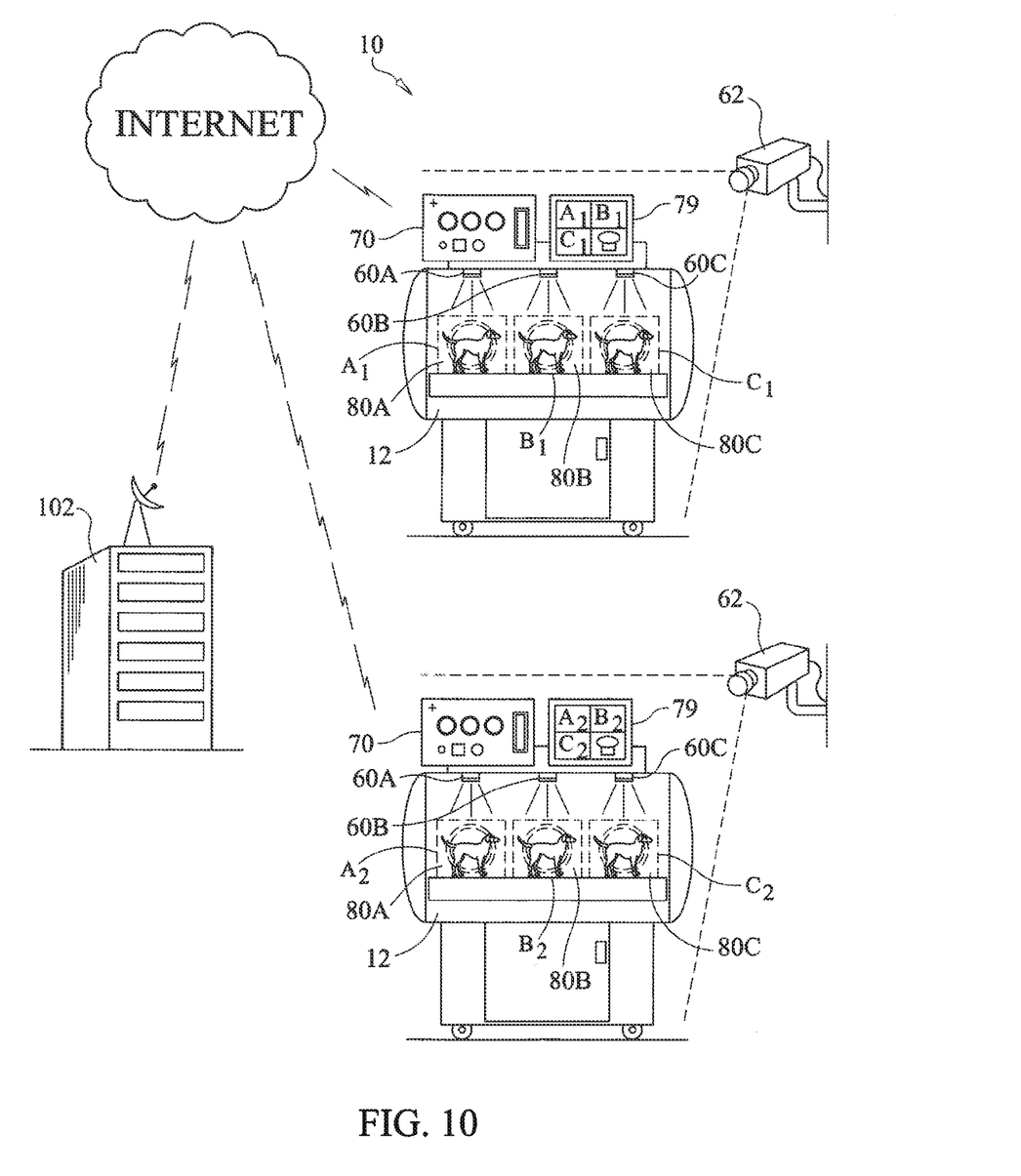
FIG. 10 is a schematic illustration of a plurality of deployed hyperbaric chambers in accordance with remote monitoring aspects of the present invention.

FIG. 10 illustrates electronic on-site and remote monitoring features in connection with a hyperbaric oxygen therapy system in accordance with the present invention. Each system 10 is provided with a closed circuit video system, including a chamber-mounted patient monitoring camera for each patient, referenced as 60A, 60B and 60C, and at least one room mounted camera 62 mounted so as to capture an external view of the pressure vessel 12. Chamber mounted cameras are positioned so as to allow for independent monitoring of each patient. In the embodiment illustrated in FIG. 10, chamber 12 is sized to treat up to 3 patients simultaneously. In an alternate embodiment, chamber 12 may be sized to handle fewer patients, such as one or two. Conversely, chamber 12 may also be enlarged to accommodate a greater number of patients, such as four, five, etc. within the scope of the present invention.

Figure 11:
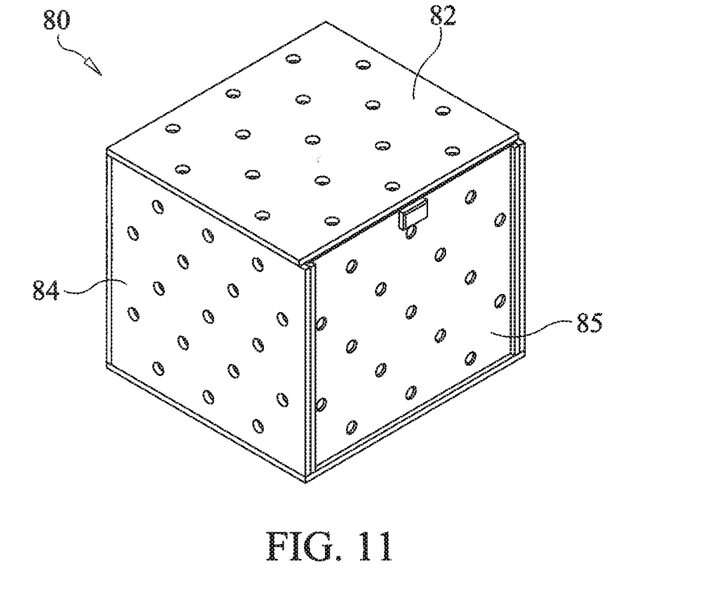
FIG. 11 is a perspective view of a pet restraint enclosure with the access door in the closed configuration in accordance with the present invention.
Figure 12:
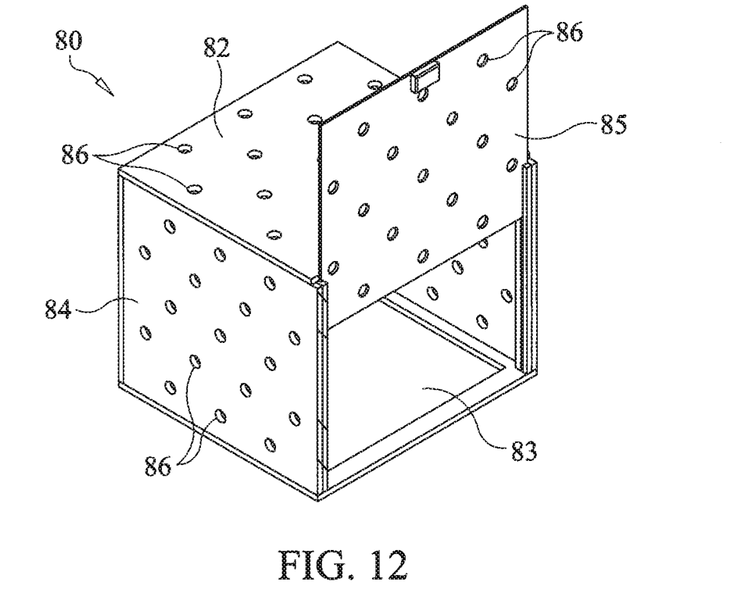
FIG. 12 is a perspective view thereof with the access door open.

FIGS. 11 and 12 depict a preferred embodiment for a pet restraint enclosure or cage, generally referenced as 80, for use with a hyperbaric chamber 10 in accordance with the present invention. As best seen in FIG. 10, each patient is confined within a transparent restraining enclosure or crate, referenced as 80A, 80B, and 80C. It is important that pet restraint enclosure 80 be fabricated from non-metallic material to prevent the formation of sparks. Pet restraint enclosure 80 is preferably fabricated from transparent plastic material, such as acrylic or Plexiglas. Enclosure 80 includes a top 82, and open bottom 83, three fixed side walls 84, and a front panel 85. Front panel 85 is configured as an openable closure whereby front panel 85 may be manually moved between a closed configuration as shown in FIG. 11 and an open configuration as shown in FIG. 12. The various panels and walls forming enclosure 80 each preferably define a plurality of ventilation apertures 86 to allow for a free flow of air through the cage. In addition, enclosure 80 preferably defines an open bottom 83 whereby the enclosure may be placed over a patient from above and removed by simply lifting the enclosure upward.

Images captured by each chamber mounted video camera 60A-60C are displayed on a visual display screen 79 mounted to chamber 12. A room mounted camera 62 is positioned so as to provide a full view of the chamber. Video streams obtained from cameras 60A-60C and room camera 62 are transmitted via suitable data transmission hardware to a remote monitoring center 102 by any suitable data transmission capability, including wired communication, wireless cellular transmission, over the Internet, etc. In addition, other data, such as chamber operating data, pressure etc. may further be transmitted. Remote central station monitoring allows for widespread deployment of hyperbaric chambers in accordance with a business method wherein revenue is generated based on usage/treatment count, such as on a per-use and/or per-patient basis. In accordance with this aspect of the present invention, a plurality of hyperbaric oxygen therapy systems 10 are deployed in veterinary clinics/facilities in various geographic areas. As used herein the term "veterinary facility" shall broadly be construed to mean veterinary clinics, hospitals, treatment centers, and other veterinary service providers. Each system 10 is installed along with a camera 62 positioned so as to enable use of the system to be remotely monitored. In accordance with this aspect of the present invention, video signals from cameras 60A-C and 62 are transmitted, via suitable wireless or wired communications link, to a remote monitoring facility 102, preferably via a global computer network, such as the Internet. As should now be apparent, personnel located at the central monitoring facility 102 are thus able to monitor each therapy session and number of patients (A, B, and C) treated per session. The monitoring feature thus enables the compilation of records confirming data relating to HBOT treatment sessions, which data preferably includes number of treatment sessions and the number of patients treated each session. In accordance with a business method of the present invention, the veterinary facilities wherein hyperbaric oxygen therapy systems 10 are deployed will be obligated to pay a royalty or fee for each use of said systems. Said fee may comprises a per-use fee (e.g. a predetermined amount for each time pressure vessel 12 is pressurized and/or each time the hatch 20 is opened and/or closed) or the fee may comprise a per-patient treated royalty wherein the number of patients (A, B, and/or C) treated provide the basis for fee calculation.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A hyperbaric oxygen therapy system for use in veterinary medicine, said system comprising:
   a pressure vessel defining an interior volume, said pressure vessel including a horizontally disposed cylindrical wall having a top, a bottom, and opposing ends including an open end and a closed end;
   a hatch hingedly connected in proximity with said open end, said hatch configurable between open and closed configurations;
   at least two viewing ports disposed on said cylindrical wall and located approximately midway between the top and bottom thereof;
   a platform slidably mounted to said pressure vessel, said platform having a front end disposed in proximity with said open end, said platform being slidably movable between a retracted position wherein said platform is contained within said interior volume, and an extended position wherein at least the front end of said platform projects from said interior volume through said open end; and
   a latching mechanism for securing said platform in said retracted position, said latching mechanism including a handle pivotally mounted to the front end of said platform, said handle movable between a normally disposed lower position and an upper position, said handle connected to a cable terminating in an anchor pin, said anchor pin disposed in an extended position when said handle is in said lower position and disposed in a retracted position when said handle is in said upper position, said anchor pin locking said platform relative to said chamber when said handle is in said lower position;
   at least two non-metallic pet restraining enclosures adapted to fit within said interior volume in side-by-side relation with each enclosure supported by said platform, said enclosures formed of transparent material and defining at least one aperture for providing ventilation;
   at least two patient monitoring video cameras mounted to said pressure vessel, each camera oriented to capture images of a patient confined within one of said pet restraining enclosures; and
   a control panel including an oxygen supply on/off switch, a plurality of pressure gauges including a line pressure gauge and a chamber pressure gauge, an oxygen flow meter, an oxygen flow regulator knob, an emergency shut-off switch, and a use counter.

2. The hyperbaric oxygen therapy system according to claim 1, further including at least one externally mounted video camera mounted external to said pressure chamber and oriented to capture images of said pressure chamber.

3. The hyperbaric oxygen therapy system according to claim 2, further including means for transmitting data from said externally mounted video camera to a remote monitoring facility.

* * * * *